United States Patent [19]
Penn et al.

[11] Patent Number: 5,641,893
[45] Date of Patent: Jun. 24, 1997

[54] CHROMATOGRAPHIC SEPARATION APPARATUS

[75] Inventors: Lynn S. Penn; Donna L. Scott, both of Lexington, Ky.; Howard H. Weetall, Rockville, Md.; Anne L. Plant, Arlington, Va.; Marion F. McCurley; Scott A. Glazier, both of Germantown, Md.

[73] Assignee: University of Kentucky Research Foundation, Lexington, Ky.

[21] Appl. No.: 605,733

[22] Filed: Feb. 22, 1996

[51] Int. Cl.$^6$ .......................... G01N 30/60; G01N 30/62
[52] U.S. Cl. ........................ 73/61.53; 73/61.58; 422/70
[58] Field of Search ........................ 73/23.39, 61.52, 73/61.53, 61.58; 422/70; 210/656; 96/106

[56] References Cited

U.S. PATENT DOCUMENTS

| | | | |
|---|---|---|---|
| 4,165,219 | 8/1979 | Huber | 436/161 |
| 4,199,260 | 4/1980 | Kusnetz et al. | 356/411 |
| 4,375,163 | 3/1983 | Yang | 73/61.53 |
| 4,575,424 | 3/1986 | Allington et al. | 210/198.2 |
| 4,734,372 | 3/1988 | Rotman | 435/291 |
| 5,164,675 | 11/1992 | Howe et al. | 325/690 |

FOREIGN PATENT DOCUMENTS

| | | | |
|---|---|---|---|
| 62-263463 | 11/1987 | Japan | 73/61.53 |

OTHER PUBLICATIONS

Kulp. Thomas J. et al.; Column–Profile Measurements Using Fiber–Optic Spectroscopy; Soil Science Society Of America Journal; vol. 52; 1988; 624–7.

Riba, J.P. et al.; Hydrodynamic Studies In Large Diameter Columns; Journal Of Chromatography; vol. 363; 1986; 113–123.

Perkins,Richard A. et al.; Fiber–Optic Fluorescence Array To Study Free Convection In Porous Media; Rev. Science Instrum.; vol. 60, No. 11; Nov. 1989; 3492–7.

Farkas, Tivadar et al; Column Efficiency & Radial Homogeneity In Liquid Chromatography; Journal Of Chromatography; vol. 679; 1994; 231–45.

Seitz, W. Rudolf; Chemical Sensors Based On Fiber Optics; Department Of Chemistry, University Of New Hampshire; Analytical Chemistry; vol. 56, No. 1; Jan. 1984.

Angel. S. M.; Optrodes: Chemically Selective Fiber–Optic Sensors; Spectroscopy; vol. 2, No. 4; Date Unknown; 38–47.

Evans, Christine E. et. al.; Dual On–Column Fluorescence Detection Scheme For Characterization Of chromatographic Peaks; American chemical Society; vol. 60; 1988.

Baur, John E. et al.; Radial Dispersion From Commercial High Performance Liquid Chromatography Columns Investigated With Microvoltammetric Elec.; A. Chem. Soc.; V. 60; 1988; 2334.

(List continued on next page.)

*Primary Examiner*—Michael Brock
*Attorney, Agent, or Firm*—King & Schickli

[57] ABSTRACT

An apparatus for the monitoring of a column chromatography separation process includes a segmented column with a seal positioned at the joint defined by the segments of the column. A connector is provided for connecting the segments of the column together. The apparatus further includes a sensor for monitoring an analyte in an eluant within a separation zone of the column. The sensor includes a mesh grid made of optical fibers or metal wires which is placed so as to extend through the separation zone of the column. The metal wires or optical fibers extend through the seal of the joint in the segmented column and connect to signal processing and data analysis equipment for purposes of monitoring the movements and concentration of an analyte in an eluant at various locations within the column. Certain segments of the optical fibers or metal wires which make up the mesh grid are coated so as to be desensitized and other segments are uncoated for sensing the analyte. This provides an effective apparatus to monitor in detail the cross-section of a column chromatography process in-situ.

24 Claims, 3 Drawing Sheets

OTHER PUBLICATIONS

Luo, S. et al; Avidin–Biotin Coupling As a General Method For Preparing Enzyme-Based Fiber–Optic Sensors; American Chemical Society; vol. 61; 1989.

Bhatia, S.K. et al.; Fiber Optic–Based Immunosensors: A Progress Report; SPIE (Society Of Photo–Optic Instrum. Engineers); vol. 1054; 1989; 184–90.

Milanovich, F. P. et al.; Remote Detection Of Organochloride With a Fiber Optic Based Sensor; Analytical Instrumentation; vol. 15, No. 2; 1986; 137–47.

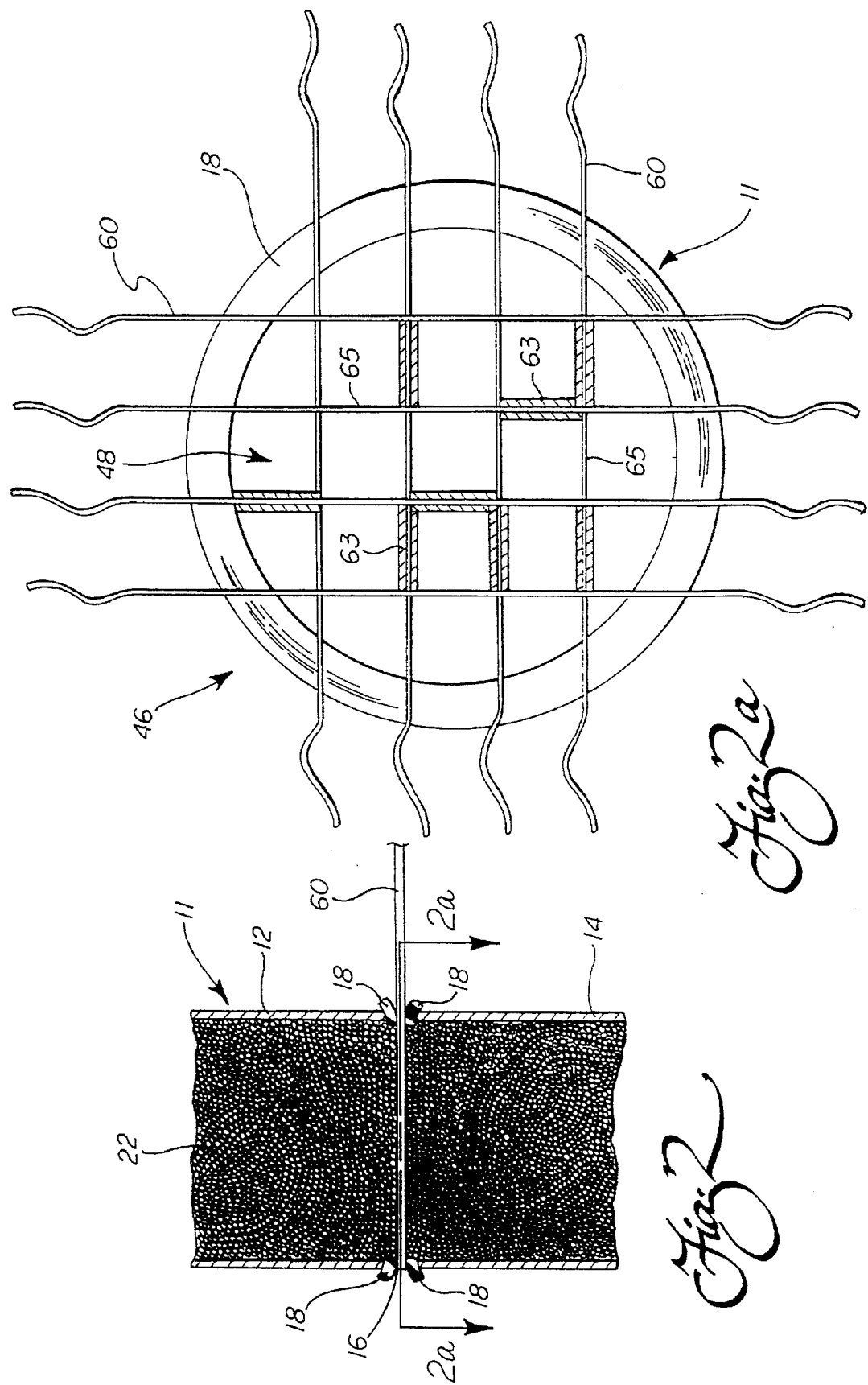

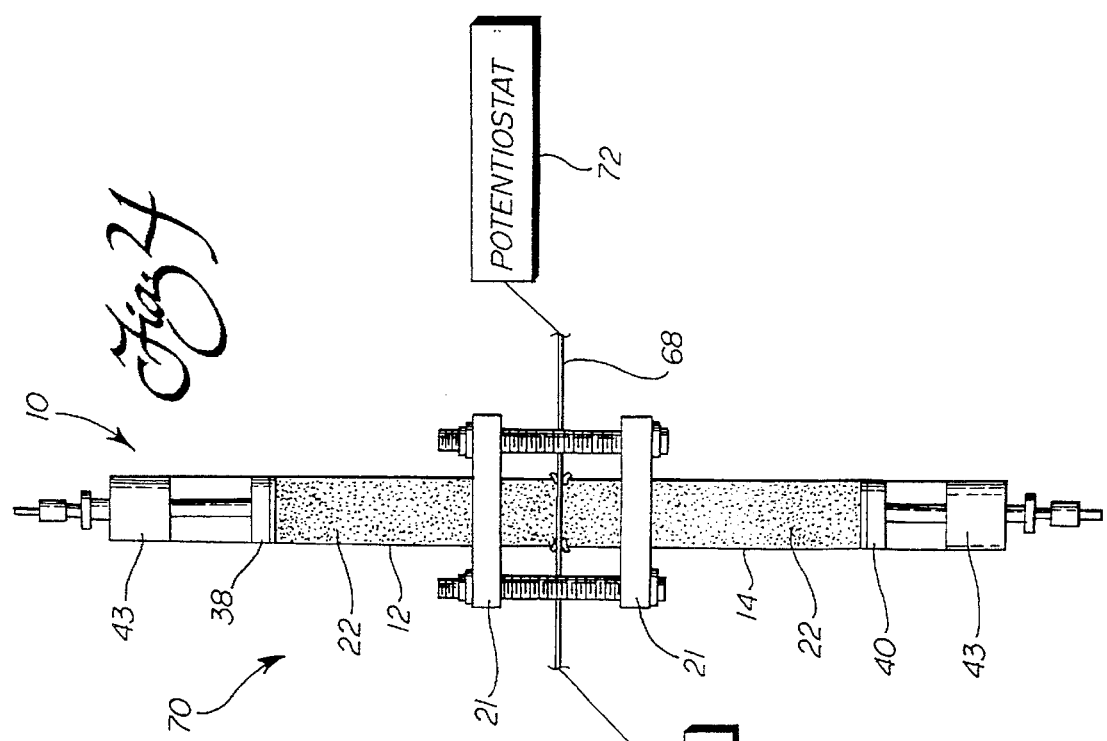
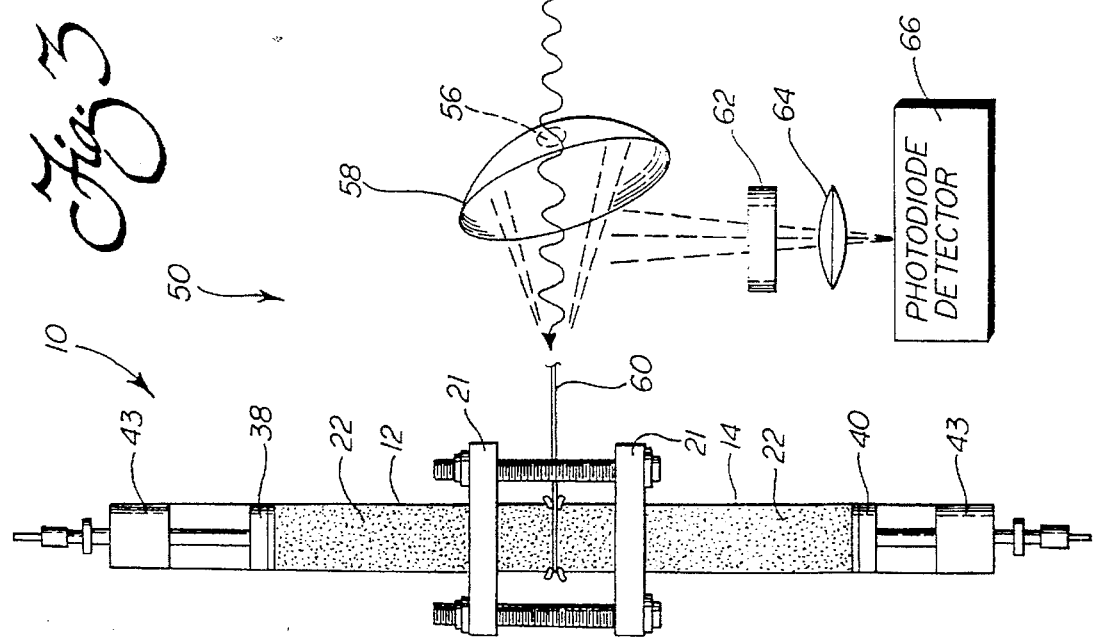

CHROMATOGRAPHIC SEPARATION APPARATUS

TECHNICAL FIELD

The present invention relates generally to column chromatography and more particularly, to an apparatus for monitoring a selected analyte in an eluant within the column during the chromatography process.

BACKGROUND OF THE INVENTION

Column chromatography provides an excellent means for separating an analyte from other chemical species in a solution. Column chromatography is a separation technique which requires a solvent as the mobile phase and a finely divided solid packing medium as the stationary phase. The molecules of the analyte to be separated interact with the stationary phase but presumably not to the same extent as molecules of other chemical species present in the solution. Thus, when the solution is introduced to the packing medium and is flushed through with eluant, the analyte and various other chemical species present in the original solution distribute themselves between the solvent (the mobile phase) and the stationary phase. The relative time required to pass through the stationary phase varies for the analyte and the other chemical species, thereby providing for separation.

Equally important as an understanding of what is taking place during the column chromatography process is the ability to accurately monitor the process. In other words, ascertaining existing column conditions during separation can provide much useful information such as how best to prepare a column and complete the separation process with the utmost efficiency. State of the art technology provides for the monitoring of several conditions during the column chromatography process. These are, for example, measurement of pH, pressure, conductivity, and UV-absorbing species at inlet and outlet positions of the column.

U.S. Pat. No. 4,165,219 to Huber provides an example of state of the art technology for monitoring a column chromatography process. The Huber patent discloses a device for analyzing solutions utilizing a chromatographic column, a metering device and a detector cell. The detector cell is positioned at the outlet of the chromatography column. While somewhat useful, it must be appreciated that the device in Huber only allows monitoring after a separation is completed. Thus, it fails to provide any specific information about the dynamics of the separation process itself. Such information would be invaluable in understanding the separation process so that a column providing for more efficient separation of a selected analyte may be developed. It should therefore be appreciated that current monitoring systems suffer from significant limitations and shortcomings that need to be overcome.

More specifically, while inlet and outlet monitoring provides information for corrective action downstream or in subsequent batches, the purification system as a whole remains passive. In addition, inlet and outlet monitoring fails to capture or identify many of the important effects that occur within the column itself. These effects include, for example, boundary distortions or band broadening caused by nonequilibrium phenomena at the column inlet and outlet, development of reaction zones among interacting components in the column, and development of gradients and inhomogeneities during the chromatographic process. All of these effects can cooperate to reduce the overall efficiency of the column.

Thus, it is clear that the present technology is inadequate in providing an effective means for monitoring the conditions within the column during the separation process. Such real time monitoring of a selected analyte and other chemical species inside a chromatography column would prove useful in column performance studies, in process or method development, and in process control and validation. Furthermore, a detailed knowledge of conditions inside the column and the flow of analytes and other chemical species of interest, as well as, key impurities, is the first step toward active, intelligent process control.

In an effort to overcome the limitations described above, new techniques are being developed for monitoring conditions within a chromatography column during the separation process. More specifically, optical fibers and metal wires are currently used for transmittal of signals generated by the presence of selected analytes within a column. This has shown to be an effective means for monitoring some conditions within the column chromatography process.

For example, the article titled "Column-Profile Measurements Using Fiber Optic Spectroscopy", published in *Soil Science Society of American Journal*, Volume 52, 624–7 (1988), discusses the desirability of being able to make measurements to identify flow patterns within a column and making such measurements using fiber optic technology. In addition, the article "Hydrodynamic Studies in Large Diameter Columns", published in *Journal of Chromatography*, Volume 363, No. 1, 113–23 (1986), discusses using metal wire sensors for studying conditions within the column during the chromatography process.

More particularly, this technology provides for the insertion of an optical fiber or metal wire into a column through an entry port. These entry ports are only large enough to allow for the insertion of a single optical fiber or wire, i.e. one sensor per entry port.

While providing a competent means for in-column monitoring, there are nonetheless still limitations and shortcomings which need to be addressed. For example, with only a single monitoring point established at each port, virtually no flexibility for altering monitoring locations is provided. Specifically, columns with entry ports are specially made and therefore, it would be necessary to reconfigure and construct a new column each time new monitoring locations are desired. In effect only one type of monitoring for a particular chemical species may be completed at each port. This severely limits the useful application of this type of technology.

In addition, state of the art technology, which utilizes optical fibers or metal wires as sensors, further reduces monitoring flexibility by failing to provide any means for effectively adjusting the relative position of the separation zone with respect to the column and entry ports. Thus, it is clear that state-of-the-art approaches are somewhat restricted or limited to monitoring a particular analyte at only certain designated points within the column. Accordingly, the overall value of the real-time information obtained is likewise restricted or limited.

SUMMARY OF THE INVENTION

Accordingly, it is a primary object of the present invention to provide a chromatographic separation apparatus allowing the dynamic monitoring of ongoing chromatographic separations and purifications in-situ overcoming the above described limitations and disadvantages of the prior art.

Still another object of the present invention is to provide a chromatographic separation apparatus for real time monitoring of various analytes and other chemical species and/or other conditions at various locations inside a chromatography column. Further, this is done with a flexibility of design heretofore unobtainable that allows one to effectively customize a single apparatus to meet the monitoring requirements of a large number of processing applications as required.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved chromatographic separation apparatus allowing for the dynamic monitoring of chromatographic separations and purifications is provided. The apparatus includes a segmented column containing a packing medium, a seal for sealing the joint defined between the segments of the column and a connector for holding the segments of the column together. The segmented column defines a separation zone within the column where the chromatographic separation process takes place.

The chromatographic separation apparatus also includes flow adapters which are attached to the opposing ends of the segmented column. The first flow adapter, which is located on the upstream side of the column, includes an entry port by which a chemical sample in solution form is delivered to the separation zone of the column for separation and purification. An eluant is also delivered to the separation zone through the entry port. Additionally, the first flow adapter includes a body for sealing the upstream end of the column.

The apparatus further includes a second flow adapter which is located on the downstream end of the column. Identical in construction to the first flow adapter, the second flow adapter includes a body for sealing the downstream end of the column and an exit port in the body for discharging the eluant and any chemical species carried thereby through the separation zone of the column.

Advantageously, the flow adapters provide an effective means for defining the relative position of the separation zone within the column. As described in greater detail below, the volumetric capacity and position of the separation zone in the column may be adjusted by simply moving or sliding the flow adapters within the column and then sealing them into position.

The chromatographic separation apparatus also includes a sensor for monitoring analytes and conditions within the column. More specifically, the sensor extends through the joint created by the segments of the column and is thus positioned within the separation zone. Accordingly, it should be appreciated that this allows for effective monitoring of the chromatographic separation process in the column and not just at the inlet and outlet of the column. This advantageously allows one to monitor separation dynamics during the actual separation process. Further, since the position of the separation zone may be adjusted relative to the position of the joint and, therefore, the monitor within the column, monitoring may be completed at substantially any spacial point in the separation zone. This is a very important feature of the present invention that is particularly useful when seeking, for example, to identify the existence of any boundary distortions, band broadening and reaction zones.

Of course, the nature and shape of the sensor may also be tailored to meet the needs of any specific application. For example, the sensor may take the form of an open planar mesh grid which extends across the internal diameter of the chromatography column. The plane of the mesh grid is perpendicular to the flow direction in the column. Each of the interstices of the mesh grid is preferably many times greater than the particle size of the packing medium. This ensures that the mesh grid does not interfere with or alter flow through the column, thereby minimizing any interference of the monitoring process with the natural dynamics of the separation process.

In a first embodiment, the mesh grid is composed of optical fibers. In an alternative second embodiment the mesh grid is composed of metal wires. In either embodiment the grid may comprise spatially arranged sensitized segments. Certain segments of the grid contain an impermeable coating so as to be desensitized to the analyte being monitored. Other segments remain uncoated or may be derivatized with a sensing chemical or recognition material for sensing the presence of the analyte. Thus, it is possible to prepare the mesh grid with spatially arranged segments so that the sensing capabilities are established at predetermined or preselected locations. It is thereby possible to customize the monitoring arrangement as desired and, for example, simultaneously monitor conditions within the column adjacent the central axis and/or along the wall.

The optical fibers or metal wires comprising the mesh grid pass through the joint of the segmented column and project outside of the column. From there, a signal may be transmitted from within the column to the signal processing and data analysis equipment located outside the column. More specifically, if optical fibers are used to form the mesh grid, then the optical fibers are connected to a light source and a light detector for analyzing the information obtained from within the column. In the alternative embodiment where metal wires are used to form the mesh grid, the signal processing and data analysis equipment may include a potentiostat for applying a potential and an ammeter for measuring the resulting current or a potentiometer for applying a voltage and an ammeter for measuring the resulting current.

Advantageously, it should be also appreciated that the chromatography column can be composed of several segments with an open planar mesh grid sensor arrangement positioned within the column at each joint. Furthermore, as previously mentioned, the flow adapters provide a means for defining or repositioning the separation zone with respect to the column. If the separation zone is repositioned, then the resulting effect is that the relative position of the mesh grid sensors are repositioned also. Accordingly, this allows one to monitor the column simultaneously at virtually an infinite number of positions within the separation zone.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 2 is a detailed partially sectional view showing a typical joint of the segmented column;

FIG. 2a is a detailed cross-sectional view along line 2a—2a of FIG. 2 showing the mesh grid sensor arrangement of the present invention;

FIG. 3 is a schematical diagram showing the signal processing system used in conjunction with the chromatographic separation apparatus of the present invention; and FIG. 4 is a schematical diagram of an alternate embodiment of the present invention.

Figure 1:
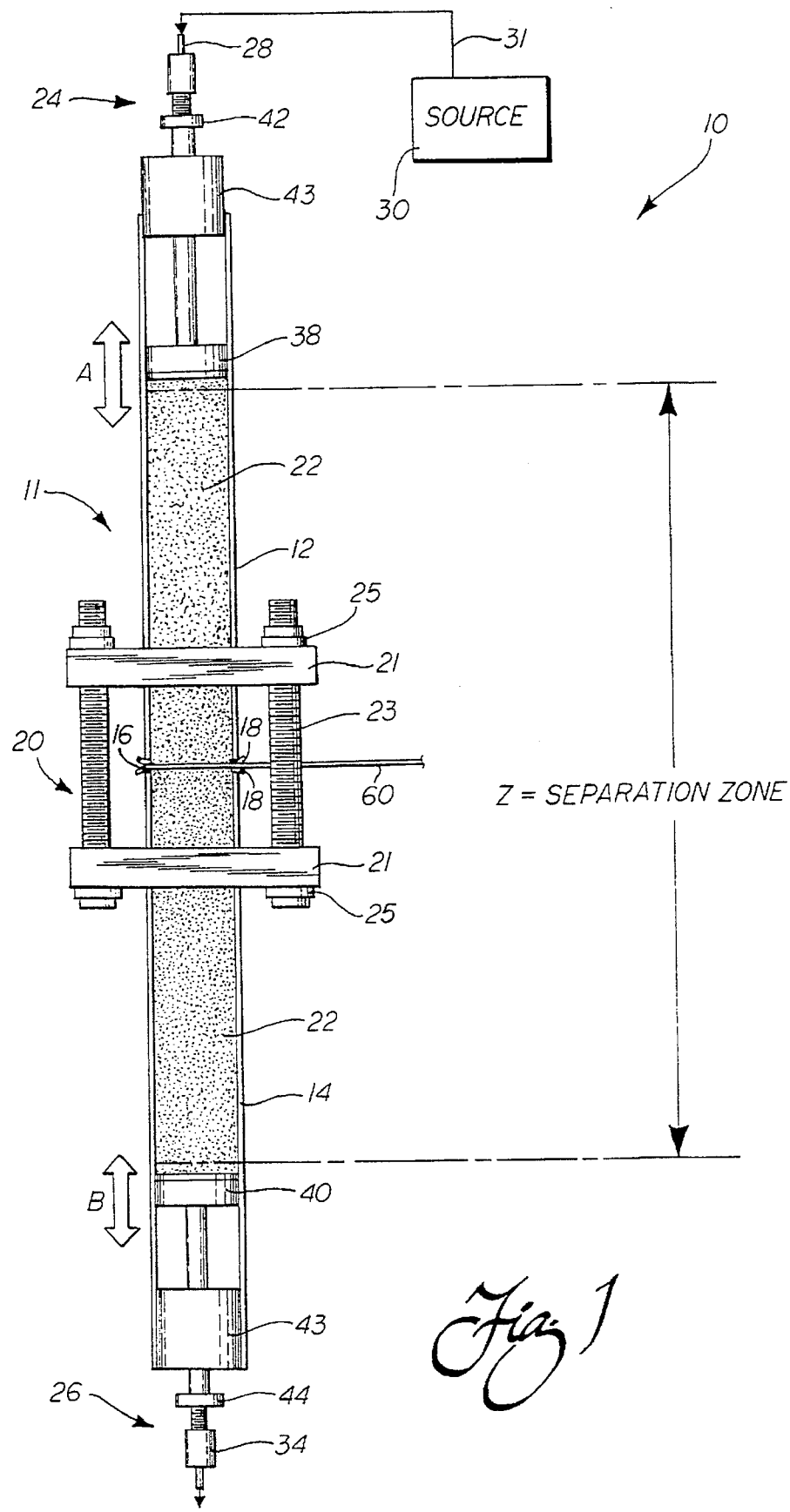
FIG. 1 is a schematical and partially sectional side elevational view of the chromatographic separation apparatus of the present invention.

Reference will now be made in detail to the present preferred embodiment of the invention, an example of which is illustrated in the accompanying drawing.

DETAILED DESCRIPTION OF THE INVENTION

Reference is now made to the drawing figures showing the chromatographic separation apparatus 10 of the present invention. As best shown FIG. 1, the chromatographic separation apparatus 10 includes a chromatography column 11 having a first column segment 12 and a second column segment 14. As is known in the art, chromatography columns can be of various shapes and sizes and are fabricated from a number of materials, such as, for example, links of glass or acrylic tube.

The first column segment 12 and second column segment 14 are axially aligned and butted together to form the chromatography column 11. A joint 16 is created where the segments 12, 14 butt together. A seal is established at joint 16 using, for example, a pair of soft elastomeric gaskets 18 (as best shown in FIG. 2). These gaskets 18, may, for example, be formed from DAP silicone sealant as manufactured by Dow Chemical Corporation of Midland, Mich.

The chromatographic separation apparatus 10 further includes a connector 20 for holding together first column segment 12 and second column segment 14. Preferably, the connector 20 comprises a pair of cooperating collars 21. One collar 21 is adhesively bonded to the outside surface of each of the first and second column segments 12, 14. The collars 21 are then fastened together by means of bolts 23 and cooperating nuts 25, the bolts 23 extending through cooperating aligned holes in the collars 21. Such a connector 20 is, for example, available from Plastic Piping Systems of Maryland, Inc., of Columbia, Md.

It should be appreciated that the first column segment 12, second column segment 14, gaskets 18 and connector 20 all must be assembled so as not to (a) interfere with the ability to pour a uniform column and (b) alter the flow of an analyte and eluant through the column 11. Otherwise, column fluidics would be affected and the results obtained from monitoring the chromatographic process would not be accurate and reliable.

Flow adapters 24, 26 (such as sold by Fisher Scientific of Pittsburgh, Pa. under Catalog No. K420415-2500) are used in conjunction with column 11 and are received therein to seal the opposing ends of the column. More specifically, first flow adapter 24 is attached to the upstream side of first column segment 12. The first flow adapter 24 includes an entry port 28 for delivering a solution containing an analyte and for delivering the eluant from a source 30 via feed line 31 into the column 11. In addition, second flow adapter 26 is attached to the downstream side of second column segment 14. The second flow adapter 26 includes a discharge port 34 for discharging eluant and analyte conveyed thereby from the column 11. Together, the sidewall of the column 11 and the flow adapters 24, 26 define the separation zone Z where the separation and purification process takes place.

This separation zone Z is filled with a solid adsorbent or packing medium 22 of a type well known in the art. This is typically accomplished by use of a gravity flow method or a pressure pumping method. The volume of packing medium 22 utilized generally falls within a range of from 90–160 ml. Numerous types of media exist for packing a chromatography column and the preferred and alternative embodiment described herein uses, for example, Sephadex G-50 gel filtration beads having a diameter in the range of 101–303 micrometers (Sigma of St. Louis, Mo.).

As should be appreciated from viewing FIG. 1, the distal end of first flow adapter 24 includes a plunger 38 located within first column segment 12. By manipulating the adjustment mechanism 42, the plunger 38 is movable in both forward and reverse directions relative to the mounting block 43 and column 11, as shown by action arrow A. Likewise, by manipulating the adjustment mechanism 44, the plunger 40 of the second flow adapter 26 is also movable in both forward and reverse directions relative to the mounting block 45 and column 11, as shown by action arrow B. Accordingly, the flow adapters 24, 26 by means of the plungers 38, 40 provide an effective means for manipulating the relative position of the separation zone Z with respect to column 11. As will be described in more detail below, this feature allows one to selectively position a sensor within the separation zone so as to monitor an analyte in-situ during ongoing processing.

As further shown, the chromatographic separation apparatus 10 also includes a sensor arrangement 46, best shown in FIG. 2a, which extends through joint 16 into the separation zone Z. This provides a means for the effective monitoring of conditions within column 11 during the chromatographic process. Advantageously, the sensor arrangement 46 may be constructed in substantially any shape from any selected material. Thus, the sensor arrangement 46 may be readily customized to meet the needs of substantially any application.

The use of a specially tailored sensor arrangement 46 in conjunction with segmented column 11 overcomes limitations and shortcomings of the prior art by providing a chromatographic separation apparatus 10 structured to allow for the monitoring of an analyte at one or several points within the column 11 and not just at the inlet and outlet. In other words, the present invention provides a chromatographic separation apparatus 11 having a flexibility of design previously unobtainable that allows one to effectively customize a single apparatus to meet the monitoring requirements of a large number of differing processing applications as required.

While inlet and outlet monitoring provides useful information such as, for example, measurement of pH, pressure, and conductivity, this as well as other useful information can be obtained by real-time monitoring of dynamic conditions within the column itself. Such other information may include, for example, boundary distortions or band broadening caused by non-equilibrium phenomena at the column inlet and outlet, development of reaction zones among interactive components in the column, and development of gradients and inhomogeneities during the chromatographic process. Accordingly, this information aids in column performance studies, as well as, in increasing the overall efficiency of a column.

It should be appreciated that while the chromatographic separation apparatus 10 shown in FIG. 1 includes a first column segment 12 and a second column segment 14, additional segments can be added to the apparatus with similar sensor arrangements 46 positioned at each additional joint. This adds to the overall flexibility of the present invention to effectively monitor the chromatography process since a multitude of points may be monitored both across the width as well as along the length of the separation zone Z in the column 11.

More particularly, the sensor arrangement 46 may include an open planar mesh grid 48 extending across the internal diameter of column 11 and positioned in a plane perpendicular to the direction of flow within the column. This allows for monitoring points to be established, as will be described in more detail below, at any chosen location across the cross-section of column 11.

In the preferred embodiment, the mesh grid 48 is constructed of an array of optical fibers 60. More specifically, optical fibers 60 are arranged so as to establish spatially arranged segments (as best shown in FIG. 2a). As will be described in more detail below, it is upon these spatially arranged segments that sensing capabilities are established for monitoring a selected analyte or other species in an eluant.

Designated segments of optical fiber 60 are blocked with an impermeable coating 63 (e.g. an opaque wax, silicone sealant or rubber) in order to be desensitized to the designated analyte to be monitored. In other words, the coated segments have no sensing capabilities. The remaining uncoated segments 65 of optical fiber 60 serve to sense the presence of the selected analyte. The surface of the uncoated segments 65 of optical fiber 60 are prepared in accordance with procedures well known in the art to provide for the recognition of the analyte by physical, chemical or biochemical means. More specifically, sensing capabilities may be established by chemically coupling a recognition layer involving antigen-antibody interaction to the surface of the uncoated optical fiber 60. Therefore, by correct choice of the coated segments and uncoated segments 65 of optical fiber 60, it is possible to create an array of pixels to monitor in detail the cross-section of column 11.

Once the layout is completed and the desired segments of optical fiber 60 are coated to provide desensitization at chosen points within column 11, the optical fibers are arranged into mesh grid 48 and positioned within the column for monitoring chromatographic separations and purifications using the configuration shown in FIG. 3. More specifically, FIG. 3 shows the signal processing system 50 which works in conjunction with sensor arrangement 46.

As is shown in FIGS. 2 and 2a, a multitude of optical fibers 60, which combine to form mesh grid 48, extend from within column 11 through joint 16 and project from the exterior of the column. For simplification of the illustration, however, FIG. 3 shows only one optical fiber 60 extending to the outside of column 11 for monitoring using signal processing system 50. Thus, it should be appreciated that for the preferred embodiment of FIG. 1, either: (1) a separate signal processing system 50 is used in conjunction with each individual optical fiber 60; or (2) a multiplexor arrangement is supplied so that one signal processing system 50 is capable of working in conjunction with a multitude of optical fibers 60.

As is known in the art, signal processing system 50 utilizes a laser light source 52 to send a light signal that travels through a small hole 56 in the parabolic mirror 58 before continuing on and entering the proximal end of optical fiber 60. Next, the light travels through optical fiber 60 and into separation zone Z of column 11 where it exits the fibers at the designated point or points and excites analytes in the sampling region to fluorescence. A portion of the light generated as a result of the fluorescence of the analyte enters the optical fibers 60 at the designed point or points and travels back through the fibers to the proximal end where it diverges onto the reflecting surface of parabolic mirror 58. The mirror 58 then directs the fluorescence produced light through a cutoff filter 62 and a focusing lens 64 onto the light detector 66. Accordingly, this system 50 provides an effective means for monitoring the conditions of an analyte in an eluant 30 within column 11.

The following example is presented to further illustrate the invention, but is not to be considered as limited thereto. The example sets forth the establishment of sensing capabilities on optical fibers 60 and the resulting interaction with the signal processing system 50.

EXAMPLE 1

A biological recognition element (e.g. antigen) is immobilized by chemical bonding to an optical fiber 60 stripped of its polymeric cladding. The end containing the immobilized antigen is placed across the internal diameter of segmented chromatography column 11 at joint 16, while the other end of the optical fiber extends through the wall of column 11 for delivering a signal to signal processing system 50 for photometric detection utilizing light detector 66. Once solution 30 containing an analyte is added to the chromatography column 11, via entry port 28 of first flow adaptor 24, the analyte, which is an antibody to the immobilized antigen, proceeds down the column and eventually reaches the optical fiber 60. The analyte molecules that directly contact the optical fiber surface experience the specific interaction with the antigen and bind to it. The number of analyte molecules binding with the antigen molecules is proportional to the solution concentration of analyte. Fluorescence, generated by fluorophor that has been incorporated into the antigen, is captured by the evanescent wave emerging from the fiber surface and is guided down the fiber to light detector 66. Fluorescence is quenched when antibody binds to antigen, and the diminution of the optical signal as a result of antibody binding is measured.

While the preferred embodiment provides for the use of optical fiber 60 for constructing mesh grid 48, it should be appreciated that other materials, for example, metal (e.g. copper or platinum) wires 68, are also useable in conjunction with the present invention (see FIG. 4). More particularly, planar mesh grid 48, as described above, can also be constructed of metal wires 68 having coated and uncoated segments for monitoring the conditions within chromatography column 11. When metal wires 68 are used in place of optical fibers 60, a different signal processing system is needed as shown in the alternate embodiment of FIG. 4. As above for purposes of simplifying the illustration only, a single metal wire is shown extending through column 11. It should be appreciated, however, that a group of wires in substantially any shape or arrangement could be utilized.

As is also known in the art, signal processing arrangement 70 shown in FIG. 4 includes a potentiostat 72 for applying a potential to wire 68 and an ammeter 74 for measuring the resulting current. Thus, this embodiment utilizes a different monitoring system. As an additional alternative, it should be appreciated that potentiostat 72 may be replaced with a potentiometer for applying a voltage to wire 68 while the ammeter 74 is maintained for measuring the resulting current.

The following example is presented to further illustrate the establishment of sensing capabilities on metal wires 68 and the resulting interaction with signal processing arrangement 70, but is not to be considered as limited thereto.

EXAMPLE 2

A biological recognition element (e.g. enzyme) is immobilized in a cross linked film that coats a wire 68. The end containing the immobilized enzyme is placed across the internal diameter of segmented chromatography column 11 at joint 16, while the other end is connected to the external circuitry for amperometric or potentiometric operation. The eluant 30 containing an analyte, which is the enzyme substrate, proceeds down column 11 and eventually reaches metal wires 68. The analyte molecules that directly contact the wire surface undergo an enzyme-substrate redox reaction. The number of analyte molecules participating in the redox reaction is proportional to the solution concentration of analyte. Thus, the number of redox reactions occurring is electrochemically transduced to the external circuitry where the signal is measured amperometrically or potentiometrically.

In summary, it should be appreciated that numerous benefits have been described which result from employing the concepts of the present invention. Advantageously, the chromatographic separation apparatus 10 of the present invention provides for effective real-time monitoring of dynamic conditions within a chromatography column 11 as opposed to only monitoring at the inlet and outlet of the column. By utilizing a segmented column 11 with sensor arrangement 46 positioned at joint 16, access is provided to the inner workings of the column without interfering with the separation and purification process taking place. More specifically, mesh grid 48 provides a means for establishing monitoring points at any chosen location along the cross-section of column 11. Furthermore, adjustable flow adapters 24, 26 make it possible to essentially relocate the relative position of separation zone z within column 11, thus increasing the number of locations where monitoring capability is establishable. More specifically, this provides for the ability to monitor at substantially any spatial point in the separation zone z. Thus, the present invention undoubtedly provides a unique chromatographic separation apparatus 10 which overcomes the shortcomings and limitations of prior art chromatography columns.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:
1. A chromatographic separation apparatus comprising:
   a column having first and second segments defining a separation zone;
   a seal for sealing a joint defined between said first and second segments;
   a sensor for monitoring an analyte in a solution extending through said joint into said separation zone, said sensor including a mesh grid extending across said separation zone; and
   a connector for connecting said first and second segments around said sensor so that said seal seals said joint.

2. The chromatographic separation apparatus as set forth in claim 1, wherein said column contains a packing medium.

3. The chromatographic separation apparatus as set forth in claim 2, further including first and second flow adapters connected to opposing ends of said column, said first and second flow adapters including a means for selectively positioning said separation zone within said column.

4. The chromatographic separation apparatus as set forth in claim 3, wherein said first flow adaptor includes an entry port for delivering said analyte in solution and an eluant to said separation zone and a body for sealing a first end of said column.

5. The chromatographic separation apparatus as set forth in claim 4, wherein said second flow adaptor includes an exit port for discharging said analyte, solution and eluant from said column and a body for sealing a second end of said column.

6. The chromatographic separation apparatus as set forth in claim 5, wherein said sensor includes a mesh grid extending across said separation zone of said column and means for analyzing data obtained while monitoring said analyte.

7. The chromatographic separation apparatus as set forth in claim 6, wherein said mesh grid has spatially arranged segments with some of said segments coated so as to be desensitized to said analyte while other of said segments are uncoated and sense the presence of said analyte.

8. The chromatographic separation apparatus as set forth in claim 7, further including metal wires which form said mesh grid, said metal wires extending through said seal at said joint of said first and second segments for connection to said means for analyzing data, said means for analyzing data including a potentiostat for applying a voltage and an ammeter for measuring resulting current.

9. The chromatographic separation apparatus as set forth in claim 7, further including metal wires which form said mesh grid, said metal wires extending through said seal at said joint of said first and second segments for connection to said means for analyzing data, said means for analyzing data including a potentiometer for applying a voltage and an ammeter for measuring resulting current.

10. The chromatographic separation apparatus as set forth in claim 7, further including optical fibers which form said mesh grid, said optical fibers extending thorough said seal at said joint of said first and second segments for connection to said means for analyzing data, said means for analyzing data including a light source and a light detector.

11. The chromatographic separation apparatus as set forth in claim 6, further including metal wires which form said mesh grid, said metal wires extending through said seal at said joint of said first and second segments for connection to said means for analyzing data, said means for analyzing data including a potentiostat for applying a voltage and an ammeter for measuring resulting current.

12. The chromatographic separation apparatus as set forth in claim 6, further including metal wires which form said mesh grid, said metal wires extending through said seal at said joint of said first and second segments for connection to said means for analyzing data, said means for analyzing data including a potentiometer for applying a voltage and an ammeter for measuring resulting current.

13. The chromatographic separation apparatus as set forth in claim 6, further including optical fibers which form said mesh grid, said optical fibers extending through said seal at said joint of said first and second segments for connection to said means for analyzing data, said means for analyzing data including a light source and a light detector.

14. The chromatographic separation apparatus as set forth in claim 1, further including first and second flow adapters connected to opposing ends of said column, said first and second flow adapters defining a means for selectively positioning said separation zone within said column.

15. The chromatographic separation apparatus as set forth in claim 14, wherein said first flow adapter includes an entry port for delivering said analyte in solution and an eluant to said separation zone and a body for sealing a first end of said column.

16. The chromatographic separation apparatus as set forth in claim 15, wherein said second flow adapter includes an exit port for discharging said analyte, solution and eluant from said column and a body for sealing a second end of said column.

17. The chromatographic separation apparatus as set forth in claim 16, wherein said sensor includes means for analyzing data obtained while monitoring said analyte.

18. The chromatographic separation apparatus as set forth in claim 17, wherein said mesh grid has spatially arranged segments with some of said segments coated so as to be desensitized to said analyte while other of said segments are uncoated and sense the presence of said analyte.

19. The chromatographic separation apparatus as set forth in claim 18, further including metal wires which form said mesh grid, said metal wires extending through said seal at said joint of said first and second segments for connection to said means for analyzing data, said means for analyzing data including a potentiostat for applying a potential and an ammeter for measuring resulting current.

20. The chromatographic separation apparatus as set forth in claim 18, further including metal wires which form said mesh grid, said metal wires extending through said seal at said joint of said first and second segments for connection to said means for analyzing data, said means for analyzing data including a potentiometer for applying a voltage and an ammeter for measuring resulting current.

21. The chromatographic separation apparatus as set forth in claim 18, further including optical fibers which form said mesh grid, said optical fibers extending thorough said seal at said joint of said first and second segments for connection to said means for analyzing data, said means for analyzing data including a light source and a light detector.

22. The chromatographic separation apparatus as set forth in claim 17, further including metal wires which form said mesh grid, said metal wires extending through said seal at said joint of said first and second segments for connection to said means for analyzing data, said means for analyzing data including a potentiostat for applying a potential and an ammeter for measuring resulting current.

23. The chromatographic separation apparatus as set forth in claim 17, further including metal wires which form said mesh grid, said metal wires extending through said seal at said joint of said first and second segments for connection to said means for analyzing data, said means for analyzing data including a potentiometer for applying a voltage and an ammeter for measuring resulting current.

24. The chromatographic separation apparatus as set forth in claim 17, further including optical fibers which form said mesh grid, said optical fibers extending thorough said seal at said joint of said first and second segments for connection to said means for analyzing data, said means for analyzing data including a light source and a light detector.

\* \* \* \* \*

UNITED STATES PATENT AND TRADEMARK OFFICE
CERTIFICATE OF CORRECTION

PATENT NO. : 5,641,893
DATED : June 24, 1997
INVENTOR(S) : Lynn S. Penn, et. al.

It is certified that error appears in the above-identified patent and that said Letters Patent is hereby corrected as shown below:

In Claim 6, column 10, lines 30 and 31, following the word "includes", delete [a mesh grid extending across said separation zone of said column and].

Signed and Sealed this

Thirteenth Day of January, 1998

BRUCE LEHMAN

Attest:

Attesting Officer

Commissioner of Patents and Trademarks

UNITED STATES PATENT AND TRADEMARK OFFICE
CERTIFICATE OF CORRECTION

PATENT NO. : 5,641,893
DATED : June 24, 1997
INVENTOR(S) : Lynn S. Penn et al.

It is certified that error appears in the above-indentified patent and that said Letters Patent is hereby corrected as shown below:

On the title page, item [73], should read as follows:

Board of Trustees of the University of Kentucky
  Lexington, Ky.

The United States of America as represented by the Secretary of Commerce
  Washington, D.C.

Signed and Sealed this

Fifteenth Day of February, 2000

Attest:

Q. TODD DICKINSON

*Attesting Officer*  *Commissioner of Patents and Trademarks*